United States Patent

Reissenweber et al.

Patent Number: 5,245,041
Date of Patent: Sep. 14, 1993

[54] PREPARATION OF HETEROCYCLIC-CYCLOHEXANEDIONE DERIVATIVES

[75] Inventors: Gernot Reissenweber, Boehl-Iggelheim; Winfried Richarz, Stockstadt, both of Fed. Rep. of Germany

[73] Assignee: BASF Aktiengesellschaft, Ludwigshafen, Fed. Rep. of Germany

[21] Appl. No.: 809,376

[22] Filed: Dec. 18, 1991

Related U.S. Application Data

[63] Continuation of Ser. No. 562,445, Aug. 2, 1990, Pat. No. 5,118,856, which is a continuation of Ser. No. 252,535, Oct. 3, 1988, abandoned, which is a continuation of Ser. No. 874,873, Jun. 16, 1986, abandoned, which is a continuation of Ser. No. 603,240, Apr. 23, 1984, abandoned.

[30] Foreign Application Priority Data

Apr. 23, 1986 [DE] Fed. Rep. of Germany ....... 3314816

[51] Int. Cl.$^5$ ............... C07D 309/02; C07D 335/02; C07D 335/16; C07D 213/44
[52] U.S. Cl. .................. 546/339; 546/344; 549/13; 549/427; 568/43; 568/13; 568/329; 568/340; 568/376; 568/427
[58] Field of Search ............ 546/339, 344; 549/13, 549/427

[56] References Cited

U.S. PATENT DOCUMENTS

| | | | |
|---|---|---|---|
| 3,950,420 | 4/1976 | Sawaki et al. | 564/300 |
| 4,115,204 | 9/1978 | Murtha | 203/60 |
| 5,006,158 | 4/1991 | Carter et al. | 71/98 |

*Primary Examiner*—Alan L. Rotman
*Attorney, Agent, or Firm*—Keil & Weinkauf

[57] ABSTRACT

A process for the preparation of cyclohexanedione derivatives of the general formula I

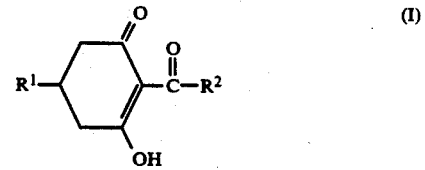

where $R^1$ is $C_2$–$C_8$-alkyl, $C_2$–$C_8$-alkenyl, $C_3$–$C_{12}$-cycloalkyl, $C_5$–$C_{12}$-cycloalkyl with 0–4 olefinically unsaturated bonds, $C_2$–$C_8$-alkylthioalkyl, $C_6$–$C_{12}$-bicycloalkyl with 0–3 olefinically unsaturated bonds, unsubstituted or substituted aryl or hetaryl, or a heterocyclic radical of 4 to 7 atoms of which not more than 3 may be hetero-atoms chosen from O, S and N, the radical being saturated or olefinically unsaturated, by reacting an $\alpha,\beta$-unsaturated ketone (II) with a dialkyl malonate in the presence of a base to give the alkoxycarbonylcyclohexenolone or its salt (III)

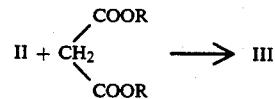

and acylation, hydrolysis and decarboxylation of (III), wherein the $\alpha,\beta$-unsaturated ketone (II) is reacted, in the presence of a base, with the dialkyl malonate in a solvent from which the alcohol liberated from the malonate can be distilled off, the alcohol is distilled off, where appropriate as an azeotrope, the salt of the alkoxycarbonylcyclohexenolone is reacted with a carboxylic acid halide and the product, where appropriate after removal of excess acyl halide, is treated with an acylation catalyst, hydrolyzed and decarboxylated.

4 Claims, No Drawings

PREPARATION OF HETEROCYCLIC-CYCLOHEXANEDIONE DERIVATIVES

This is a continuation of application Ser. No. 562,445, filed Aug. 2, 1990, U.S. Pat. No. 5,118,856, which is a continuation of Ser. No. 252,535 filed Oct. 3, 1988, abandoned, which is a continuation of Ser. No. 874,873, filed Jun. 16, 1986, abandoned, which is a FWC of Ser. No. 603,240, filed Apr. 23, 1984, abandoned.

The present invention relates to a process for the preparation of cyclohexanedione derivatives (I)

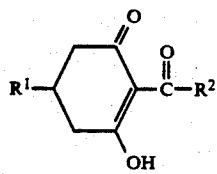

which are useful as direct intermediates in the preparation of plant growth regulators. Such regulators are described in, for example, German Laid-Open Application DOS 2,822,304 and U.S. Pat. Nos. 3,950,420 and 4,011,256. These state that the regulators ma be obtained from intermediates of type (I).

According to Tetrahedron Lett. 29 (1975), 249 and Synthesis 1978, 925, compounds (I) may be obtained from correspondingly substituted cyclohexanediones by C- or O-acylation, the O-acylation requiring a subsequent isomerization step.

As far as can be deduced from the references mentioned, the reaction is not particularly free from side reactions and accordingly the yield of the individual steps is not particularly high. The nature of the particular reactions involved moreover requires that at each stage the intermediates be isolated in a pure form and experience shows that this further reduces the overall yield.

It is an object of the present invention to provide a simple process, which can be carried out in very simple reaction vessels, for obtaining cyclohexanedione derivatives (I)

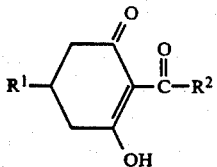

where $R^1$ is one of the radicals mentioned in claim 1 and $R^2$ is alkyl of not more than 6 carbon atoms.

We have found that this object is achieved and that compounds (I) can be obtained from simple inexpensive compounds, namely $\alpha,\beta$-unsaturated ketones (II)

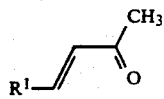

and dialkyl malonates in a single reaction vessel and in one and the same solvent, by a process wherein 1. an appropriate $\alpha,\beta$-unsaturated ketone of the formula II

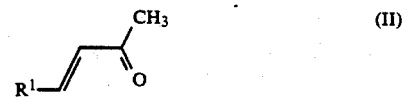

in reacted, in the presence of a base, with a dialkyl malonate in a solvent from which the alcohol liberated from the malonate can be distilled off, to given an alkoxycarbonylcyclohexenolone (III) or its salt

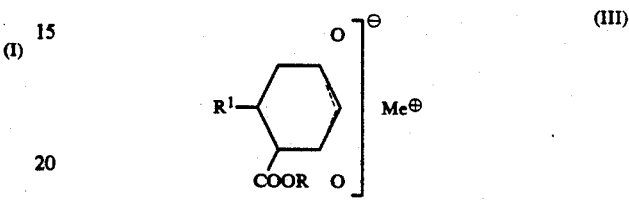

2. the alcohol is distilled off, where appropriate as an azeotrope with a part of the solvent,
3. the salt of the cyclohexenolone III is treated with a carboxylic acid halide (IV)

where $R^2$ is alkyl of, for example, not more than 6 carbon atoms, preferably methyl, ethyl or propyl, giving a mixture of cyclohexenone carboxylic acid esters (Va) and (Vb)

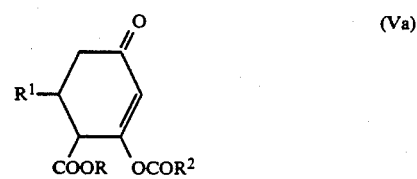

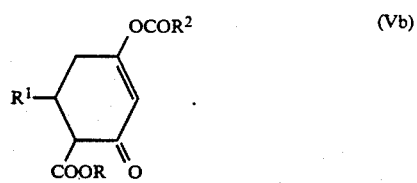

4. the mixture of the esters (Va) and (Vb) is rearranged under the action of an acylating catalyst to give the 2-acylcyclohexanedione (VI)

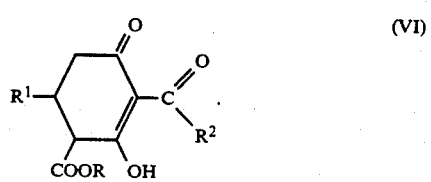

5. and this product is hydrolyzed and decarboxylated. With respect to step 1 of this process, reference is made to Org. Synth. Coll. Vol. 2,6th printing, p. 200 (John Wiley & Sons, New York, 1950).

The process is applicable to the preparation of cyclohexanedione derivatives of the formula I having the above substituents $R^1$ and $R^2$. The substituent R in the above formulae corresponds to the alkyl radical of the alcohol from which the malonate is derived and, for economic reasons, is preferably methyl or ethyl.

The solvent used is advantageously an aromatic alkylhydrocarbon or halohydrocarbon, e.g., toluene, ethylbenzene, a xylene, isopropylbenzene or chlorobenzene, an aliphatic or cycloaliphatic hydrocarbon or an ether. It must permit the distillation of, for example, methanol when using dimethyl malonate, and may not interfere with the subsequent reaction with the acyl halide. It may not be a solvent for the salt III which is formed; rather, the salt in general precipitates, for example from toluene, as a solid, i.e. a suspension is formed. This is of no disadvantage to the reaction.

Toluene is the preferred solvent when dimethyl malonate is used as a reactant, since methanol forms an azeotrope with toluene.

The unsaturated ketone and malonate are preferably used in a stoichiometric ratio; a slight excess of one or other is not particularly objectionable but a larger excess should be avoided, since it entails an additional separation step and/or involves additional distillation expense.

In the presence of an alkali metal alcoholate, for example sodium methylate, the reaction takes place even at room temperature and goes to completion as the alcohol liberated is distilled off by gradual heating. The reaction can also be carried out at a higher temperature, for example not more than 100° C.

The methanol or other alcohol must be removed as completely as possible since the acyl halide added will otherwise preferentially react with the alcohol.

The acid halide is then added to the substantially alcohol-free suspension of the salt formed and the mixture is kept at 40°-200° C., preferably 80°-160° C., in the course of which the salt dissolves and the corresponding alkali metal halide precipitates. The acid halide is also used in approximately stoichiometric amount, and is advantageously not used in excess.

Thereafter, a catalytic amount of a rearrangement catalyst is added. Examples of suitable catalysts are tertiary amines and especially pyridine bases, e.g. 4-dimethylaminopyridine, 4-piperidinopyridine, 4-morpholinopyridine or N-alkylated imidazoles or benzimidazoles. The rearrangement takes place in the same temperature range as the preceding reaction and sometimes takes place at sufficient speed even at room temperature.

Thin-layer chromatography, for example, may be used to check whether the rearrangement is complete.

Aqueous alkali metal hydroxide solution is then added and the product to be hydrolyzed goes into solution in the aqueous phase. Of course the solvent can alternatively be stripped off first, and the residue taken up in the aqueous alkali. The hydrolysis in general requires a lower temperature than the preceding reactions, for example 20°-100° C., preferably 40°-80° C. The amount of alkali metal hydroxide solution must of course be not less than 2 mole equivalents, based on ketone employed initially, since both the alkoxycarbonyl group and the mobile hydrogen of the diketone each bond 1 mole equivalent of base. A certain excess of alkali accelerates the hydrolysis, but too large an excess should be avoided since the decarboxylation remains to be carried out.

The decarboxylation is carried out in mineral acid solution or in the presence of a stronger carboxylic acid, such as formic acid or acetic acid, at from room temperature to about 100° C.

The desired cyclohexanedione derivative in general precipitates from the aqueous, acid solution and can be collected by filtration or where appropriate by extraction, and be purified, if necessary, by recrystallization.

The invention permits the preparation of compounds of type I, which hitherto were only obtainable by multistage synthesis with in part poor yields and expensive purification operations, in a simple and economical manner, in good yield, with high space-time yield and in excellent purity. It is particularly the preparation of very pure products which is especially important in the present instance, since the 2-acyl-cyclohexane-1,3-dione derivatives prepared by the process of the invention are valuable intermediates for highly active herbicidal substances (cf. German Laid-Open Applications DOS 2,822,304, DOS 2,439,104, DOS 3,032,973, DOS 3,047,924 and DOS 3,121,355 and European Patent 66,195).

EXAMPLE 1

Preparation of 2-butyryl-5-(p-toluyl)-cyclohexane-1,3-dione 132 g of dimethyl malonate are introduced into 1 liter of toluene and 180 g of 30% strength sodium methylate solution are added at room temperature. A crystal slurry results, to which 160 g of p-methylbenzalacetone are added dropwise, with vigorous stirring. In the course of 3 hours, the reaction mixture is heated, with methanol distilling off azeotropically, until the temperature at which the vapors pass over has reached 110° C. 106 g of butyryl chloride are then added at 80°-90° C. and stirring is continued briefly. 5 g of 4-N,N-dimethylaminopyridine are added, the mixture is stirred for 3-4 hours at 100° C. and the solvent is then evaporated. A solution of 120 g of sodium hydroxide in 1.5 liters of water is added to the residue and the mixture is stirred for 2 hours at 80° C. It is then acidified with 270 ml of concentrated hydrochloric acid at 60° C., and when the mixture has cooled to room temperature the precipitate is filtered off with suction and washed neutral with water. After is has been dried, 239 g (88%) of 2-butyryl-5-(p-toluyl)-cyclohexane-1,3-dione, of melting point 76°-78° C., are obtained.

EXAMPLE 2

Preparation of 2-propionyl-5-(pyrid-3'-yl)-cyclohexane-1,3-dione 132 g of dimethyl malonate are introduced into 1 liter of toluene and 180 g of 30% strength sodium methylate solution are added. 147 g of 1-pyrid-3'-yl-but-1-en-3-one are then added dropwise, with vigorous stirring. In the course of 3 hours, the reaction mixture is heated, with methanol distilling off, until the temperature at which the vapors pass over has reached 110° C. 92.5 g of propionyl chloride are then added at 80° C. and the mixture is stirred for a further hour at the same temperature. 5 g of 4-N,N-dimethylaminopyridine are added and the mixture is stirred for 4 hours at 100° C. When it has cooled to room temperature, the reaction mixture is extracted twice with a total of 1.2 kg of 10% strength sodium hydroxide solution and the alkaline extract is then stirred for 3 hours at 60° C. 365 g of 30% strength hydrochloric acid are then added to the reaction mixture and the batch is stirred for 2 hours at 50° C. When it has cooled to room temperature, the solid which has precipitated is filtered off with suction, washed with water and dried. 189 g (77%) of 2-propionyl-5-(pyrid-3'-yl)-cyclo-hexane-1,3-dione, of melting point 80°-81° C., are obtained.

EXAMPLE 3

Preparation of 2-butyryl-5-cyclohexylcyclohexane-1,3-dione 132 g of dimethyl malonate, 180 g of 30% strength sodium methylate, 152 g of 1-cyclohexylbut-1-en-3-one and 106.5 g of butyryl chloride are reacted in 1 liter of toluene, in a manner similar to that described in Example 1. 5 g of 4-N,N-dimethylaminopyridine are added to the reaction mixture thus obtained and the batch is stirred for 4 hours at 100° C. and then cooled to room temperature. It is then extracted twice with a total of 3.5 moles of sodium hydroxide in 1.5 liters of water and the combined alkaline extracts are stirred for 2 hours at 80° C. They are then acidified with about 270 ml of concentrated hydrochloric acid at 50° C., the oil obtained is extracted with methylene chloride and the extracts are washed with water and evaporated in vacuo. 222 g (84%) of 2-butyryl-5-cyclohexylcyclohexane-1,3-dione are obtained as a pale brown oil.

The compounds (I) listed in the Table which follows are examples of compounds obtainable by appropriate modification of the details in the preceding Examples:

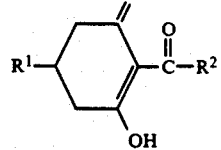

| $R^1$ | $R^2$ | Melting point | Yield |
|---|---|---|---|
| CH$_3$—CH=CH— | C$_3$H$_7$ | oil | 72% |
| 2,6,6-trimethylcyclohex-2-enyl | C$_3$H$_7$ | oil | 80% |
| 2,6,6-trimethylcyclohex-1-enyl | C$_3$H$_7$ | oil | 84% |
| 4-methylcyclohexyl | C$_2$H$_5$ | oil | 77% |
| phenyl | C$_3$H$_7$ | 64–65° C. | 86% |
| 4-methylphenyl | C$_3$H$_7$ | 72–73° C. | 92% |
| 4-chlorophenyl | C$_3$H$_7$ | | 78% |
| 4-fluorophenyl | C$_3$H$_7$ | 76–78° C. | 82% |
| pyrid-3-yl | C$_3$H$_7$ | 74–75° C. | 80% |
| pyrid-4-yl | C$_3$H$_7$ | 94–96° C. | 76% |
| tetrahydropyran-4-yl | C$_3$H$_7$ | 48–49° C. | 78% |
| 3,4-dihydro-2H-pyran-4-yl | C$_3$H$_7$ | 44–46° C. | 69% |
| 4-methyltetrahydropyran-3-yl | C$_3$H$_7$ | 49–51° C. | 72% |
| bornyl | C$_3$H$_7$ | 63–65° C. | 76% |
| bicyclic alkenyl | C$_3$H$_7$ | 54–56° C. | 72% |
| tetrahydrothiopyran-4-yl | C$_2$H$_5$ | 70–72° C. | 83% |

-continued

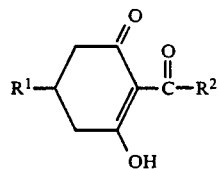

| $R^1$ | $R^2$ | Melting point | Yield |
|---|---|---|---|
| 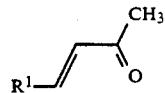 | $C_3H_7$ | 70–72° C. | 81% |
| 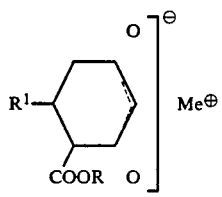 | $C_3H_7$ | oil | 86% |
| $C_2H_5-S-CH-CH_2-$<br>           $\mid$<br>           $CH_3$ | $C_3H_7$ | oil | 89% |

We claim:

1. A process for the preparation of cyclohexanedione derivatives of the formula I

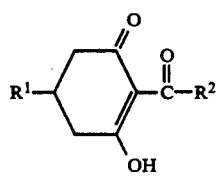

where $R^1$ is a hetero-cyclic radical of 4 to 7 atoms of which not more than 3 may be hetero-atoms chosen from O, S and N, the radical being saturated or olefinically unsaturated, and $R^2$ is alkyl of 1–6 carbon atoms, by reaction of an alpha-beta unsaturated ketone with a dialkyl malonate in the presence of a solvent, which process includes the addition of a base, a decarboxylation step, a hydrolyzation step and an acylation step, the improvement comprising: the reaction of an $\alpha,\beta$-unsaturated ketone of the formula

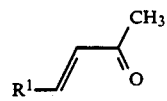

with a dialkyl malonate in the presence of a base to give the alkoxycarbonylcyclohexenolone or its salt (III)

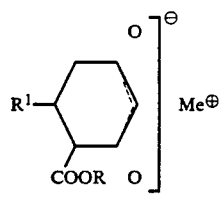

and acylation, hydrolysis and decarboxylation of (III), R being the alcohol radical of the malonate and $R^1$ having the above meaning, the process steps comprising
(a) reacting the $\alpha,\beta$-unsaturated ketone (II) in the presence of a base, with the dialkyl malonate in a solvent from which the alcohol liberated from the malonate can be distilled off,
(b) distilling to eliminate the alcohol,
(c) reacting the salt of the alkoxycarbonylcyclohexenolone with a carboxylic acid halide having the structural formula $R^2COHal$, where $R^2$ is alkyl of not more than 6 carbon atoms to form a product,
(d) treating the product of step (c), where appropriate, after removal of excess acyl halide, with an acylation catalyst, to form a further product, and
(e) hydrolyzing and decarboxylating the product of step (d) to form the compound of formula I.

2. In a process for the preparation of cyclohexanedione derivatives of the formula I

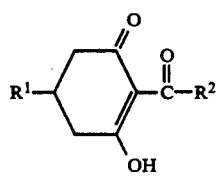

where $R^1$ is an unsubstituted or methyl-monosubstituted heterocyclic radical of 6 atoms containing one heteroatom selected from O and S, the radical being saturated or monoolefinically unsaturated; and $R^2$ is alkyl of 1 to 6 carbons, by reacting an alpha-beta unsaturated ketone with a dialkyl malonate in the presence of a solvent, which process includes the addition of a base, a decarboxylation step, a hydrolization step and a acylation step, the improvement comprising reacting an $\alpha,\beta$-unsaturated ketone of the formula II

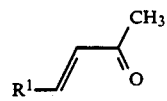

with a dialkyl malonate in the presence of a base to give the alkoxycarbonylcyclohexenolone or its alkali metal salt (III)

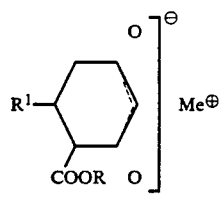

where R is the alcohol radical of the malonate and $R^1$ has the above meanings, followed by rearrangement under the action of a catalyst, by hydrolysis and by decarboxylation of (III), the process steps comprising:
(a) reacting the $\alpha,\beta$-unsaturated ketone (II) in the presence of a base with dimethyl or diethyl malonate in a solvent from which the alcohol liberated from the malonate can be distilled off,
(b) distilling off the alcohol,
(c) reacting the alkali metal salt of the alkoxycarbonylcyclohexenolone with a carboxylic acid halide $R^2COHal$, where $R^2$ is alkyl of not more than 6 carbon atoms to form a product, (d) rearranging the product of step (c) with a tertiary amine at temperatures between room temperature and 200° C., to form a further product, and
(e) hydrolyzing the product of step (d) with an aqueous alkali metal hydroxide solution to form a third product and decarboxylating the third product in the presence of a mineral acid solution or in the presence of a stronger carboxylic acid to form the compound of formula I.

3. The process of claim 2, wherein the alcohol in the step (b) is distilled off as an azeotrope and wherein the tertiary amine of step (d) is pyridine base.

4. The process of claim 1, wherein $R^1$ is pyridyl.

* * * * *

UNITED STATES PATENT AND TRADEMARK OFFICE
CERTIFICATE OF CORRECTION

PATENT NO. : 5,245,041

DATED : September 14, 1993

INVENTOR(S) : REISSENWEBER et al.

It is certified that error appears in the above-identified patent and that said Letters Patent is hereby corrected as shown below:

On the title page:
Item [30] Foreign Application Priority Data should read as follows:

--Apr. 23, 1983 [DE]  Fed. Rep. of Germany ...... 3314816--.

Signed and Sealed this

Fifth Day of April, 1994

*Attest:*

BRUCE LEHMAN

*Attesting Officer*   *Commissioner of Patents and Trademarks*